(12) United States Patent
Kim et al.

(10) Patent No.: US 11,883,509 B2
(45) Date of Patent: Jan. 30, 2024

(54) PHARMACEUTICAL COMPOSITION FOR INHALATION ADMINISTRATION FOR LABELING PULMONARY TUMOROUS LESION, CONTAINING FLUORESCENT CONTRAST AGENT AS ACTIVE INGREDIENT

(71) Applicants: KOREA UNIVERSITY RESEARCH AND BUSINESS FOUNDATION, Seoul (KR); KOREA ADVANCED INSTITUTE OF SCIENCE AND TECHNOLOGY, Daejeon (KR)

(72) Inventors: Hyun Koo Kim, Seoul (KR); Yuhua Quan, Seoul (KR); Byeong-Hyeon Choi, Seoul (KR); Ji-Yun Rho, Incheon (KR); Ji Ho Park, Daejeon (KR); Ji Young Lim, Daejeon (KR); Chan Hee Oh, Daejeon (KR); Daeho Jung, Daejeon (KR)

(73) Assignees: Korea University Research and Business Foundation, Seoul (KR); Korea Advanced Institute Of Science And Technology, Daejeon (KR)

( * ) Notice: Subject to any disclaimer, the term of this patent is extended or adjusted under 35 U.S.C. 154(b) by 628 days.

(21) Appl. No.: 16/561,069

(22) Filed: Sep. 5, 2019

(65) Prior Publication Data

US 2020/0101175 A1    Apr. 2, 2020

(30) Foreign Application Priority Data

Sep. 5, 2018 (KR) .................. 10-2018-0106037
Sep. 2, 2019 (KR) .................. 10-2019-0108377

(51) Int. Cl.
*A61B 17/00* (2006.01)
*A61K 49/00* (2006.01)
*A61K 9/00* (2006.01)

(52) U.S. Cl.
CPC ........ *A61K 49/0034* (2013.01); *A61K 9/0078* (2013.01)

(58) Field of Classification Search
CPC .................. A61K 9/0078; A61K 9/007; A61B 17/00234; A61B 2017/00238; A61B 2017/00261
See application file for complete search history.

(56) References Cited

FOREIGN PATENT DOCUMENTS

WO   WO 2014/186909 A1    11/2014
WO   WO-2014186909 A1 *   11/2014   ......... A61K 49/0084

OTHER PUBLICATIONS

Hofstetter et al (Aerosol Delivery During Mechanical Ventilation to the Rat; Experimental Lunch Research, vol. 30, Issue 7, 2004). (Year: 2004).*
Moghissi et al (Image-guided surgery and therapy for lung cancer: a critical review; Future Oncology, 2017, vol. 13, Issue 26, 2383-2394) (Year: 2017).*
R. Baumgartner et al (Inhalation of 5-aminolevulinic acid: a new technique for fluorescence detection of early stage lung cancer; Journal of Photochemistry and Photobiology B: biology 36, 169-174, 1996 (Year: 1996).*
Onda, Nobuhiko et al., "Preferential tumor cellular uptake and retention of indocyanine green for in vivo tumor imaging", *International Journal of Cancer 2016*, vol. 139, Issue 3, 2016 (pp. 673-682).
Korean Office Action dated Feb. 3, 2021 in counterpart Korean Patent Application No. 10-2019-0108377 (7 pages in Korean).

* cited by examiner

*Primary Examiner* — Micah Paul Young
(74) *Attorney, Agent, or Firm* — NSIP Law

(57) ABSTRACT

The present disclosure relates to a method for providing information for determining lung tumor through inhalation of a fluorescent contrast agent, more particularly to a method of inhaling a small amount of Indocyanine green. The present disclosure does not have the problem of the existing intravenous injection that the administered fluorescent contrast agent is distributed throughout the body. In addition, when comparing the cancer detection efficiency of inhalation administration and intravenous injection, the inhaled fluorescent contrast agent exhibits remarkably higher cancer detection effect than the intravenously injected fluorescent contrast agent.

5 Claims, 7 Drawing Sheets

[FIG. 1a]
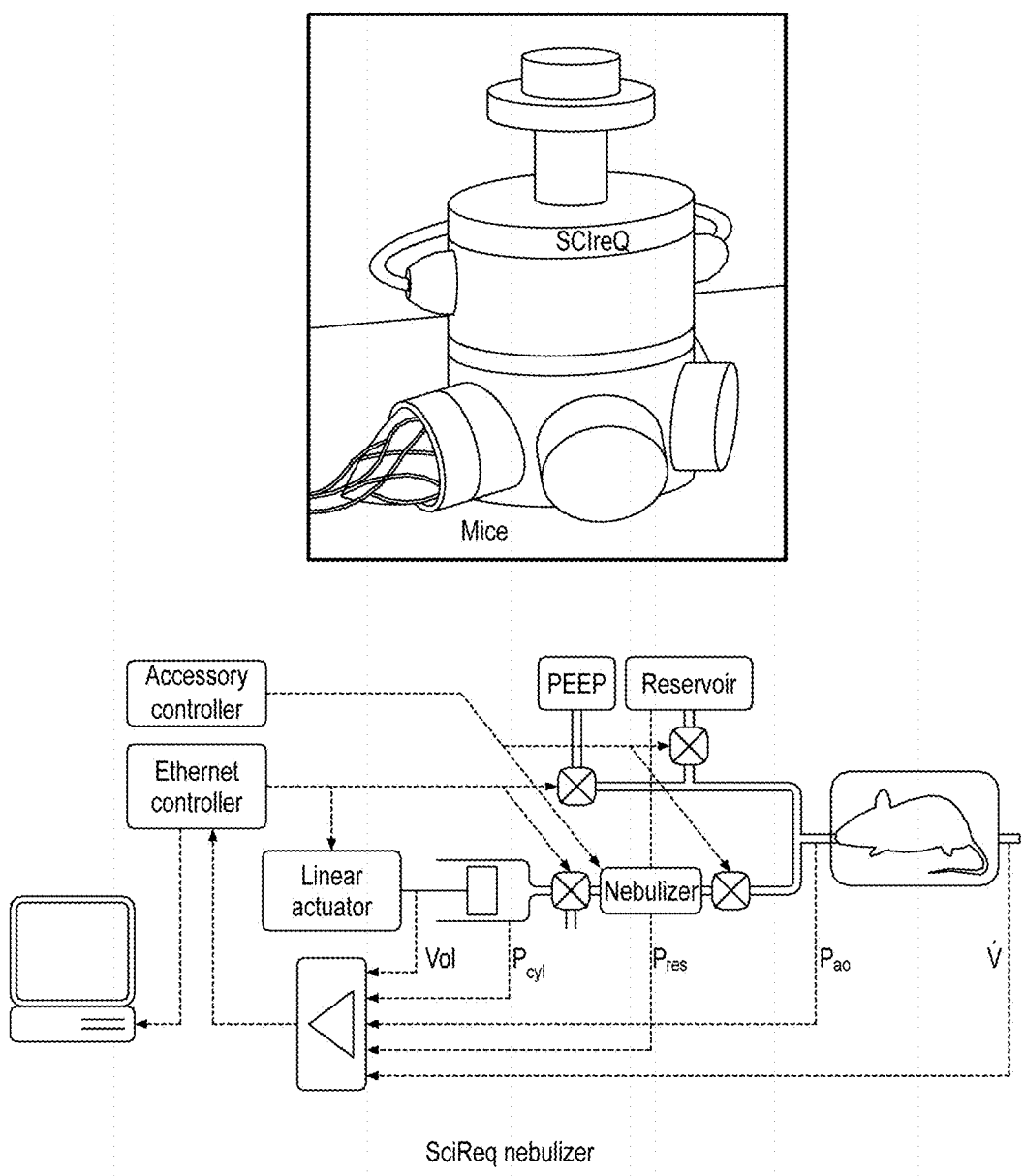

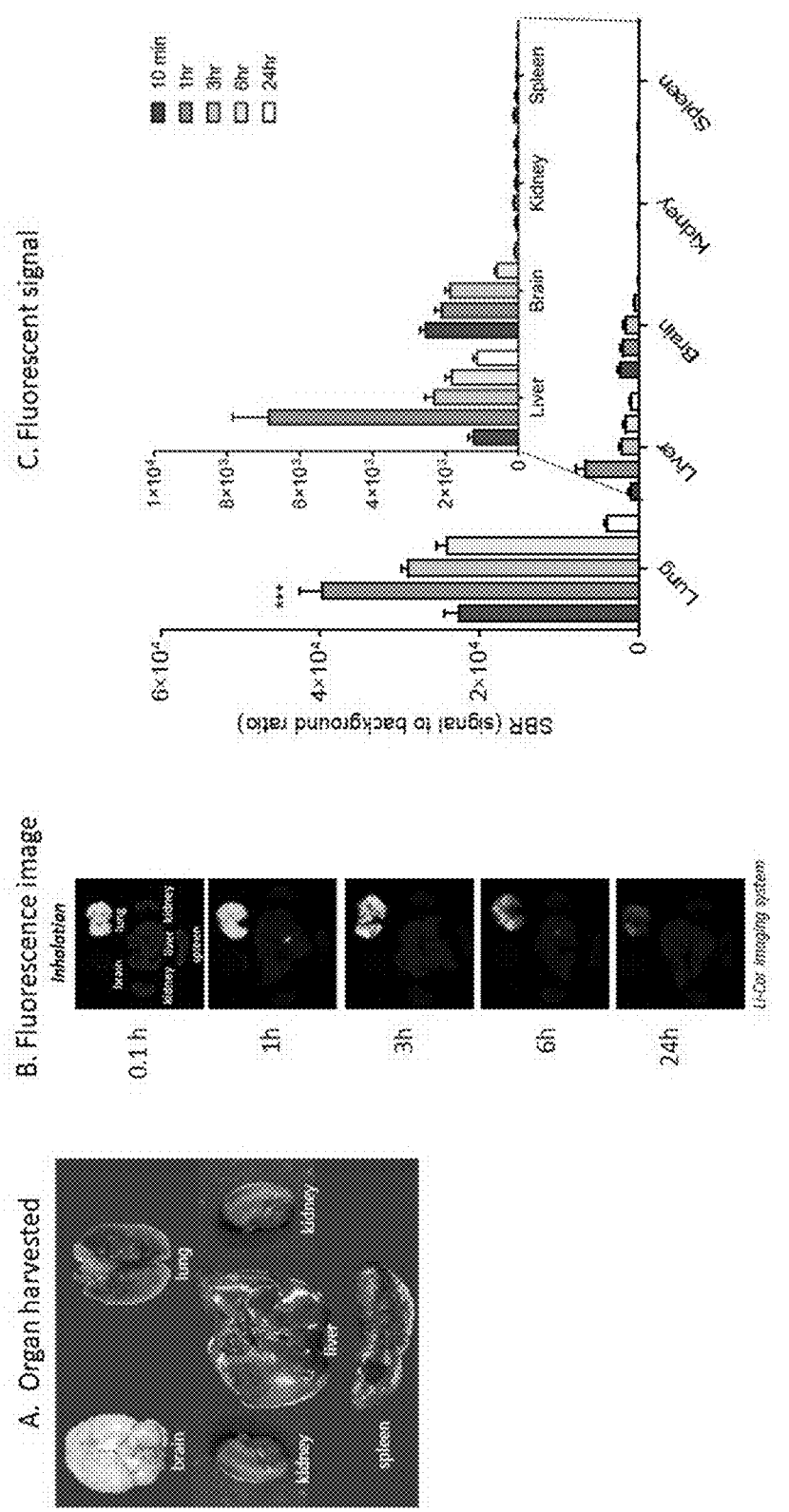
[FIG. 1b]

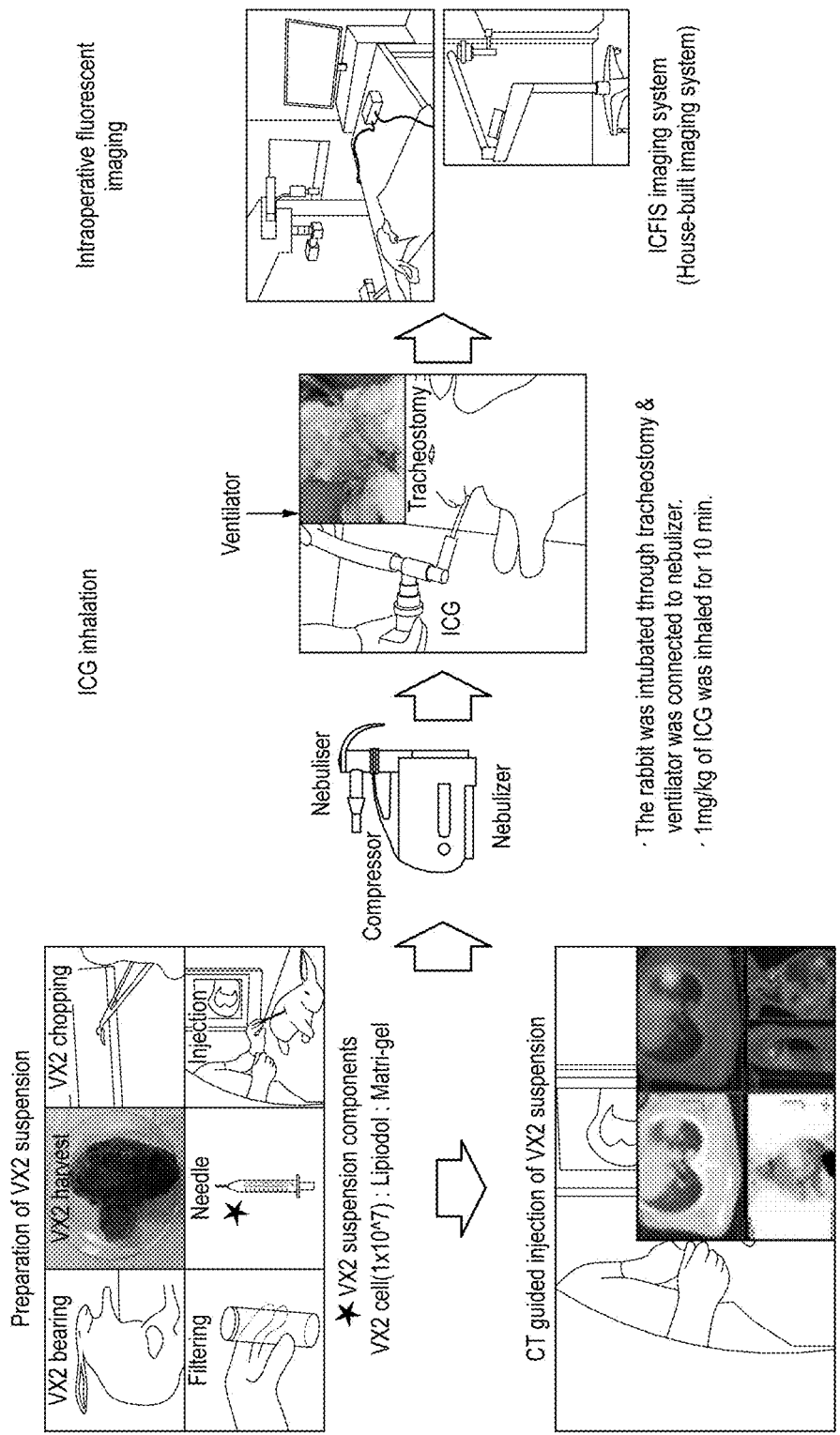
[FIG. 2a]

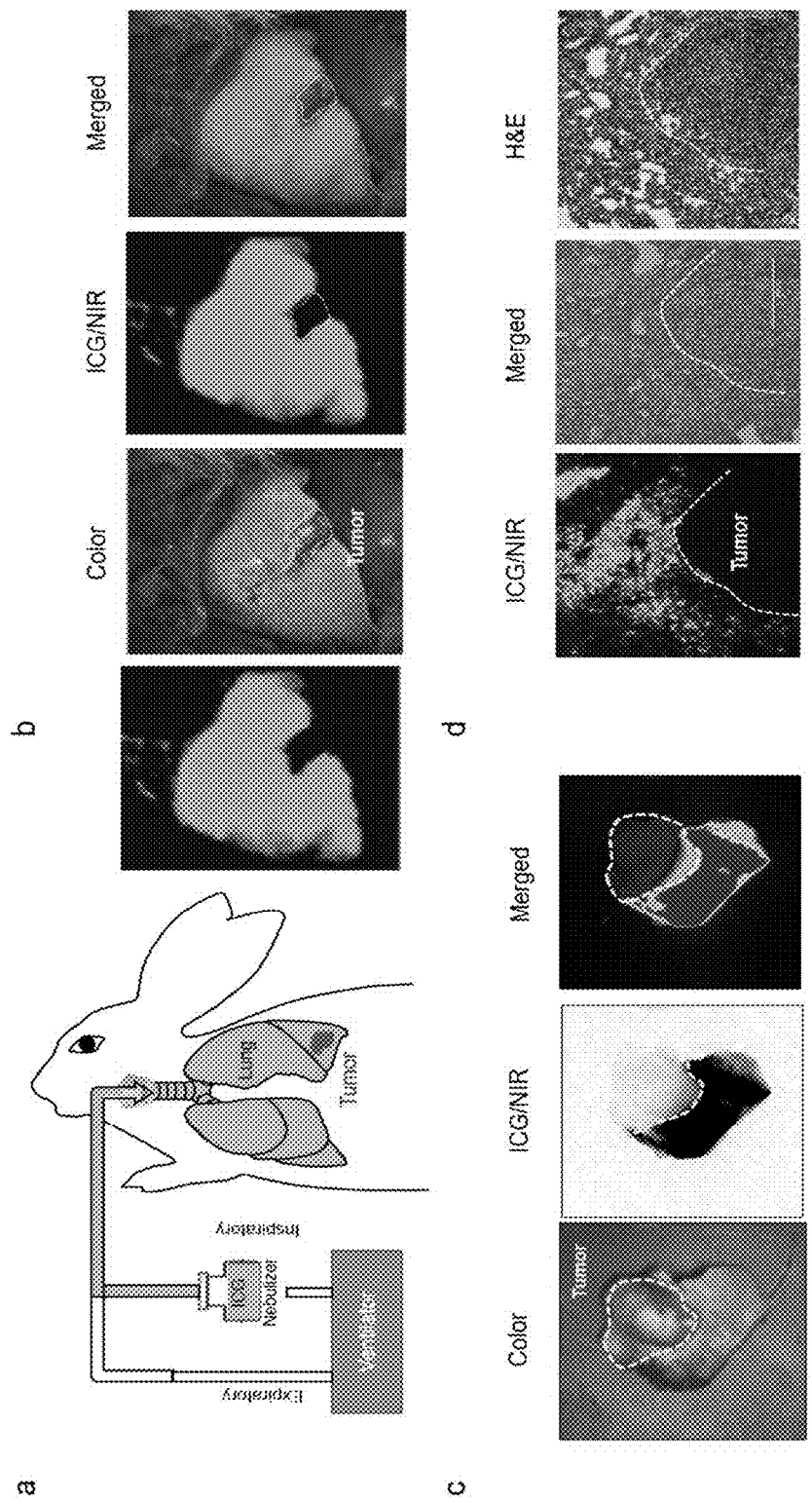
[FIG. 2b]

[FIG. 2c]
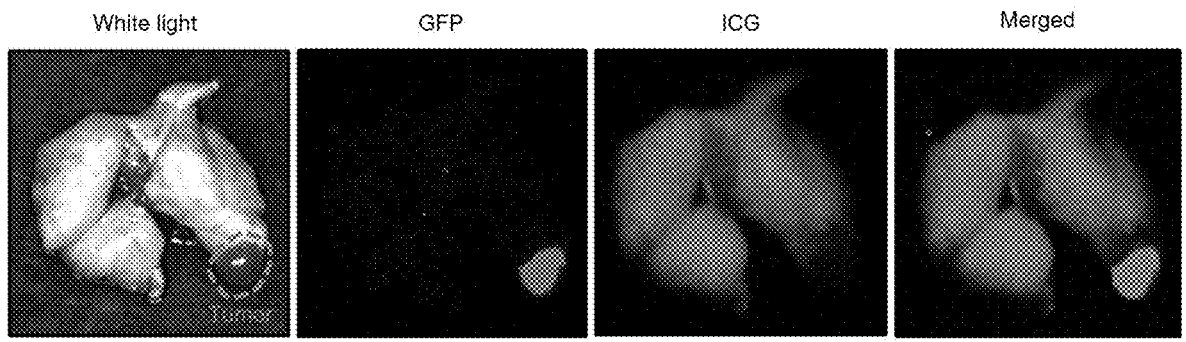
[FIG. 3]
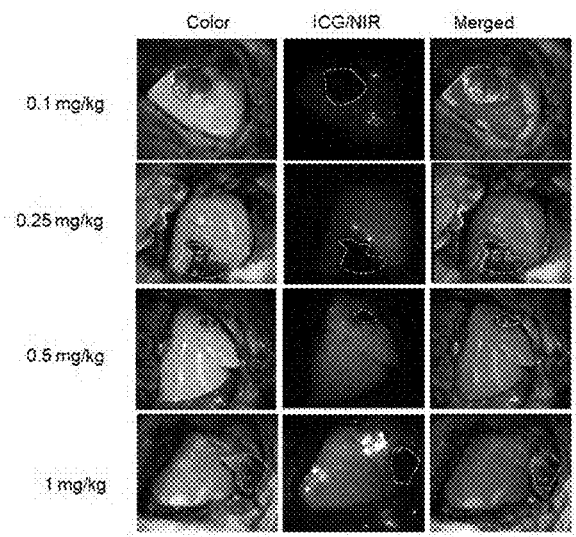
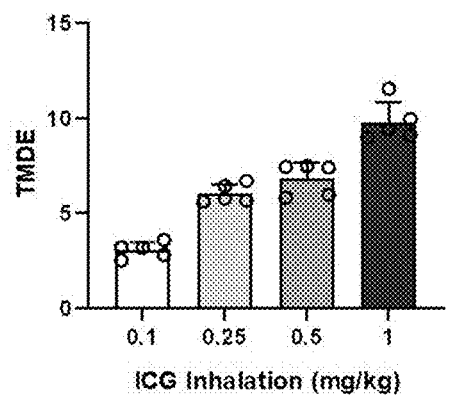

[FIG. 4a]
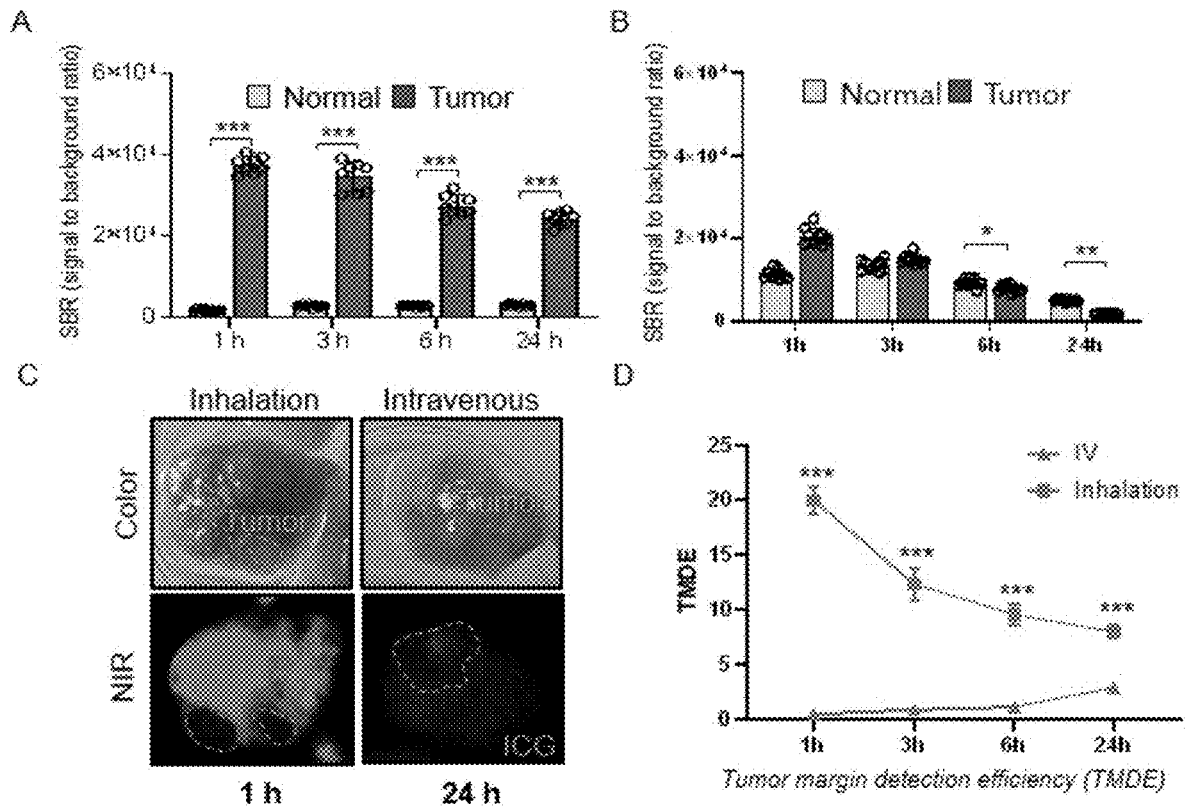
[FIG. 4b]
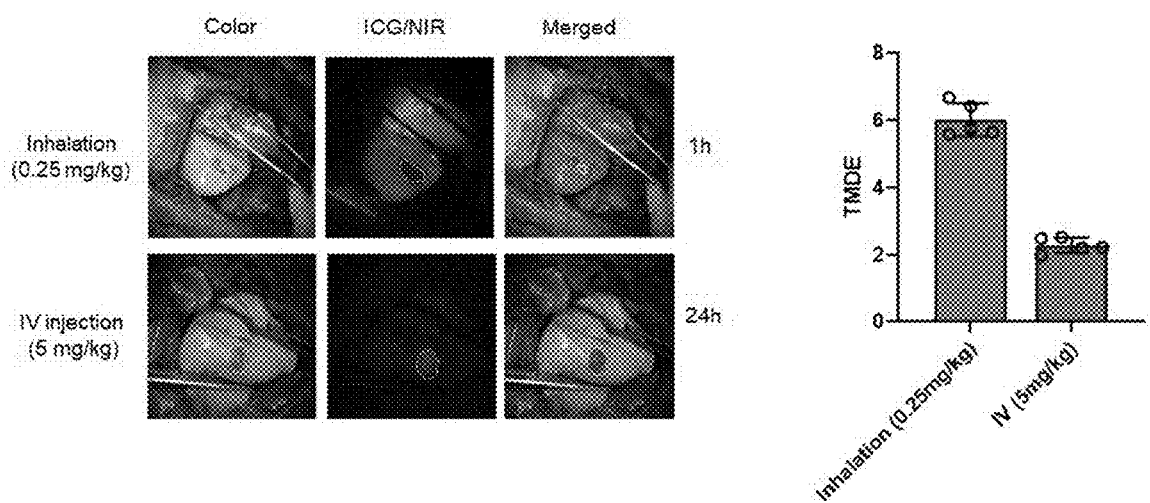

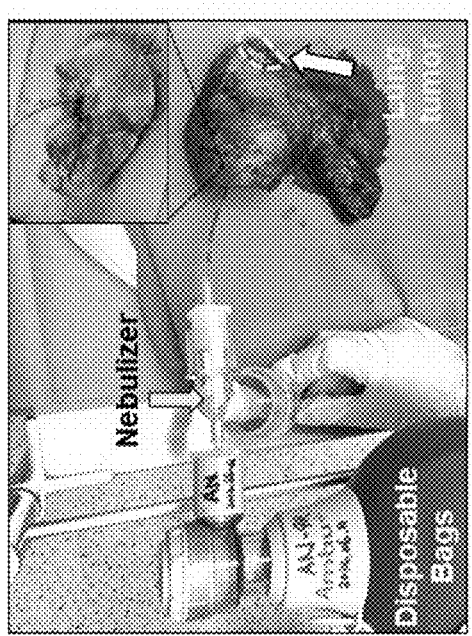
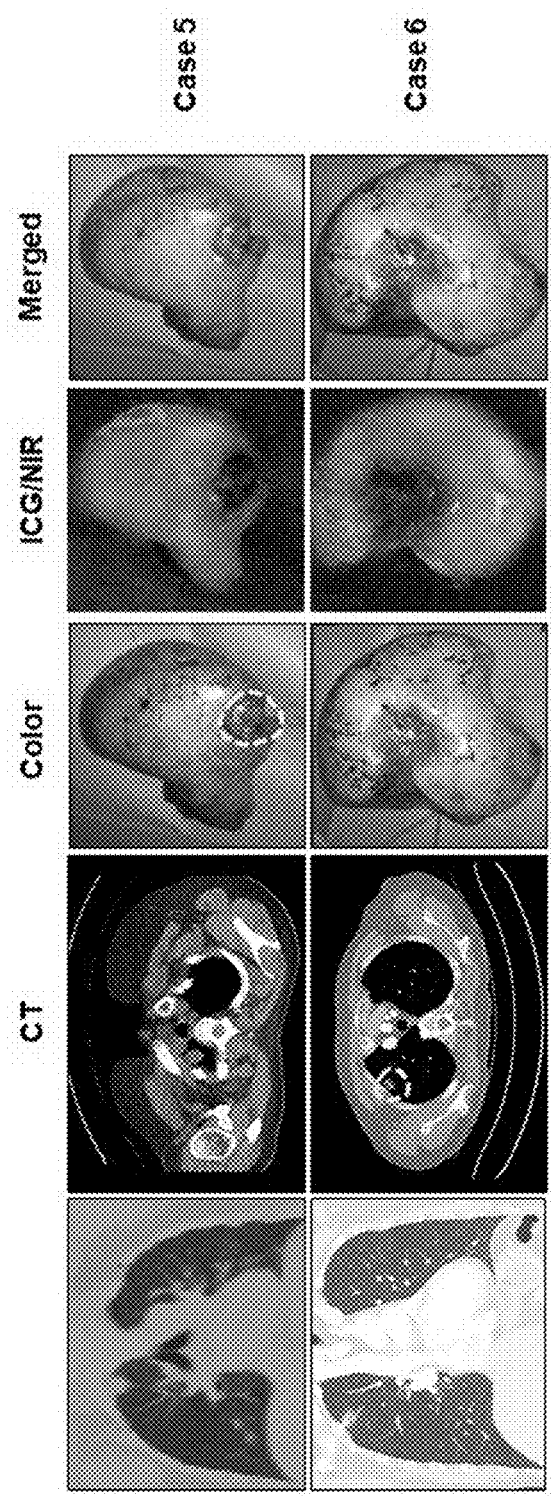
[FIG. 5]

PHARMACEUTICAL COMPOSITION FOR INHALATION ADMINISTRATION FOR LABELING PULMONARY TUMOROUS LESION, CONTAINING FLUORESCENT CONTRAST AGENT AS ACTIVE INGREDIENT

CROSS REFERENCE TO RELATED APPLICATION(S)

This application claims the benefit under 35 USC § 119(a) of Korean Patent Application No. 10-2018-0106037 filed on Sep. 5, 2018 and Korean Patent Application No. 10-2019-0108377 filed on Sep. 2, 2019 in the Korean Intellectual Property Office, the entire disclosure of which is incorporated herein by reference for all purposes.

TECHNICAL FIELD

The present disclosure relates to a pharmaceutical composition for inhalation administration for labeling pulmonary tumorous lesion, which contains a fluorescent contrast agent as an active ingredient.

BACKGROUND ART

The cancers occurring the most frequently in Koreans are stomach cancer, colon cancer, lung cancer, thyroid cancer and liver cancer. According to the national statistics on cancer, the risk of developing cancer in lifetime is increasing with 1 out of 3 in men, and 1 out of 4 in women. In particular, with the aggravation of air pollution due to industrialization and increase of smokers, particularly juvenile and female smokers, it is expected that the number of patients with lung cancer will increase. In the US, too, lung cancer is the most common cause of cancer-related death in men and women.

The two main types of lung cancer are small-cell lung cancer (SCLC) and non-small-cell lung cancer (NSCLC). Small-cell lung cancer (SCLC) is a fast-growing type of lung cancer. It spreads much more quickly than non-small-cell lung cancer. There are three different types of small-cell lung cancer: small-cell carcinoma (oat cell cancer), mixed small-cell/large-cell carcinoma, and combined small-cell carcinoma. Most of the small-cell lung cancer is oat cell type. Non-small-cell lung cancer (NSCLC) is the most common type of lung cancer. There are three types of NSCLC: adenocarcinoma, squamous cell carcinoma, and large-cell carcinoma. Adenocarcinoma occurs mainly peripheral lung tissues. It occurs frequently even in women or non-smokers and is metastasized often. Recently, the frequency of occurrence is increasing. Next, squamous cell carcinoma is mainly found in the center portion of the lung. It grows mainly toward and block the bronchial lumen. It occurs frequently in men and is known to be closely related with smoking. Large-cell carcinoma occurs mainly around the surface (periphery) of the lung and about half occurs in the large bronchus. It accounts for about 4-10% of lung cancer. The cell size is generally large and some show worse prognosis than other non-small-cell lung cancers due to fast proliferation and metastasis. The common therapies for lung cancer include palliative care, surgery, chemotherapy and radiotherapy.

If diagnosed in the early stage, lung cancer can be recovered through medication, radiation therapy, etc. However, if the symptoms worsen to certain levels, surgical treatment is essential, and chemotherapy and radiotherapy are used together. But, the rate of early diagnosis of lung cancer is not high as about 20%. Accordingly, most of lung cancer patients receive surgery for pulmonary nodules. Considering the structural characteristics of the lungs, it is important to accurately identify the location and size of lesion and minimize excision during surgery for pulmonary nodules.

Meanwhile, near-infrared fluorescence imaging is drawing attentions as an imaging technology for noninvasive diagnosis and monitoring of diseases. The near-infrared region of 700-900 nm allows ideal bioimaging because of the advantages that background autofluorescence is weak, light scattering is less and imaging is possible for deep tissues. Among the fluorescent dyes for fluorescence imaging, Indocyanine green (ICG) is a near-infrared fluorescent dye approved through clinical trials. It is mainly used for staining of liver blood vessels and heart, and various diagnosis and imaging applications.

Since the finding in 1999 during intravenous injection of Indocyanine green for surgery that the boundary of liver cancer can be detected by near-infrared fluorescence imaging, passive targeting fluorescent contrast agents that can be used for clinical applications are actively used for cancer detection.

However, for cancer detection, the fluorescent contrast agent should be intravenously injected at a high concentration of at least 5 mg/kg. Although it is used indiscriminately for various cancers, including colon cancer, breast cancer, skin cancer, lung cancer, etc., the detection rate is very low for lung cancer. Specifically, the cancer detection rate for lung cancer is reported to be merely 10% because the cancer tissues are mainly located at a depth of 1 cm or greater from the lung surface.

The inventors of the present disclosure have researched on a method capable of detecting the boundary of cancer tissue more accurately during surgery for pulmonary nodules and have completed the present disclosure.

REFERENCES OF RELATED ART

Non-Patent Documents (Non-patent document 0001) Int J Cancer. 2016 Aug. 1; 139(3): 673-82. doi:10.1002/ijc.30102.

DISCLOSURE

Technical Problem

The present disclosure is directed to providing the information about the size and/or location of lesion more accurately and effectively during surgery for pulmonary nodules by administering a fluorescent contrast agent via respiration of a subject. It is directed to providing a pharmaceutical composition for inhalation administration for labeling pulmonary tumorous lesion, which contains a fluorescent contrast agent as an active ingredient, a kit and an inhalant for labeling pulmonary tumorous lesion, a method for providing information for determining a pulmonary tumorous lesion site, and a method for identifying the boundary of lesion during surgery for pulmonary nodules.

However, the technical problem to be solved by the present disclosure is not limited to that mentioned above and other problems not mentioned above will be clearly understood by those of ordinary skill in the art from the following description.

Technical Solution

The present disclosure provides a pharmaceutical composition for inhalation administration for labeling pulmonary tumorous lesion, which contains a fluorescent contrast agent as an active ingredient.

The present disclosure also provides a pharmaceutical composition for inhalation administration for labeling lung cancer lesion, which contains a fluorescent contrast agent as an active ingredient.

In an exemplary embodiment of the present disclosure, the pharmaceutical composition may contain 6-30 mg of a fluorescent contrast agent and may be effective for once-daily administration. Specifically, it may contain 15 mg of a fluorescent contrast agent and may be effective for once-daily administration.

The present disclosure also provides a kit for labeling pulmonary tumorous lesion, which contains the pharmaceutical composition.

In an exemplary embodiment of the present disclosure, the kit may be used for identifying the size and location of cancer tissue in real time during surgery for pulmonary nodules.

The present disclosure also provides an inhalant for labeling pulmonary tumorous lesion, which contains a fluorescent contrast agent as an active ingredient.

In an exemplary embodiment of the present disclosure, the inhalant may contain 6-30 mg, specifically 15 mg, of a fluorescent contrast agent.

The present disclosure also provides a method for providing information about the location and/or size of pulmonary tumorous lesion, which includes: (a) a step of injecting a fluorescent contrast agent into the lungs via respiration of a subject; (b) a step of detecting a fluorescence signal generated by the contrast agent using a fluorescence imaging system; and (c) a step of determining a region where the fluorescence signal is not detected as a tumor tissue.

In an exemplary embodiment of the present disclosure, in the step (a), the fluorescent contrast agent may be injected in an amount of 0.1-0.5 mg per unit body weight (1 kg) of the subject, specifically 0.25 mg per unit body weight of the subject.

In another exemplary embodiment of the present disclosure, the injection in the step (a) may be performed using a nebulizer.

The present disclosure also provides a method for identifying the boundary of lesion during surgery for pulmonary nodules, which includes: (1) a step of administrating a fluorescent contrast agent via respiration of a subject; (2) a step of cutting open the chest of the subject and detecting a fluorescence signal generated by the contrast agent using a fluorescence imaging system; and (3) a step of determining a region where the fluorescence signal is not detected as a lesion and a region where the fluorescence signal is detected as a normal tissue.

In an exemplary embodiment of the present disclosure, the subject may be human and/or a mammal except for human.

In another exemplary embodiment of the present disclosure, the lesion may be a damaged alveolar structure. Specifically, it may be an alveolar structure damaged due to proliferation of tumor cells or cancer cells.

In another exemplary embodiment of the present disclosure, in the step (1), the fluorescent contrast agent may be administered in an amount of 0.1-0.5 mg per unit body weight (1 kg) of the subject, specifically 0.25 mg per unit body weight of the subject.

In another exemplary embodiment of the present disclosure, the administration in the step (1) may be performed using a nebulizer.

In the present disclosure, the fluorescent contrast agent may be one or more selected from a group consisting of Indocyanine green (ICG), Alexa Fluor 647, Alexa Fluor 660, Alexa Fluor 680, Alexa Fluor 700, Alexa Fluor 780, cy3.5, cy5, cy5.5, cy7, Cypate, ITCC, NIR820, NIR2, IRDye78, IRDye80, IRDye82, IRDye680, IRDye700, IRDye800, DiD, DiR, Cresy Violet, Nile Blue, Oxazine 750, Rhodamine800, Texas Red and a mixture thereof.

The present disclosure also provides a use of a fluorescent contrast agent for preparation of a pharmaceutical composition for inhalation administration or an inhalant for labeling a lung tumor lesion.

The present disclosure also provides a method for diagnosing lung tumor, which includes the steps (1) to (3).

The present disclosure also provides a method for surgery for pulmonary nodules, which includes the steps (1) to (3).

Advantageous Effects

The present disclosure relates to an administration method and administration dosage of a fluorescent contrast agent, which is capable of providing information about the location and/or size of tumor tissue accurately and effectively. The present disclosure does not have the problem of the existing intravenous injection that the administered fluorescent contrast agent is distributed throughout the body. Because the location, size, etc. of cancerous lesion quickly and accurately in real time at a smaller dosage than intravenous injection, the success rate of the surgical operation of pulmonary tumorous lesion can be improved. In addition, it can be widely used for effective anticancer therapies because excessive loss of normal tissue can be prevented.

BRIEF DESCRIPTION OF DRAWINGS

FIG. 1a schematically illustrates an experiment for investigating the distribution of ICG administered via the airway in the body. FIG. 1b shows that the ICG administered via the airway is located particularly in the lungs, emits fluorescence within 10 minutes after the administration and emits maximum fluorescence after 1 hour, and that the fluorescence is maintained for 24 hours.

FIG. 2a shows a method of preparing a lung tumor-induced rabbit model and a process of acquiring information about the location and size of pulmonary tumorous lesion by administering ICG via the airway. FIG. 2b shows fluorescence images and H&E staining images acquired from the lungs of a rabbit which inhaled ICG. FIG. 2c shows GFP-labeled lung cancer cells and the distribution of ICG administered via respiration.

FIG. 3 compares the degree of staining and cancer detection rate in a lung tumor-induced rabbit model depending on the concentration of ICG administered via the airway.

FIG. 4a and FIG. 4b compare the degree of staining and cancer detection rate in a lung tumor-induced rabbit model depending on the administration route of ICG (airway administration and intravenous administration).

FIG. 5 shows a result of identifying the boundary of lesion after administering ICG into human lungs via the bronchus. It can be seen that the boundary of cancer tissue is consistent with the pathological outcome.

BEST MODE

The inventors of the present disclosure have researched to solve the problem of low lung tumor detection rate of intravenous administration of a fluorescent contrast agent and have completed the present disclosure.

The inventors of the present disclosure have predicted that, when considering the structural characteristics of the lungs, inhaled nanosized substances will reach normal alveoli but they will not reach the pneumothorax or lung tumor due to the damage of the alveolar structure. They have investigated cancer detection efficiency, etc. by administering a fluorescent contrast agent which is generally administered intravenously into the alveoli via the airway. As a result, they have identified that, when the fluorescent contrast agent Indocyanine green (ICG) is administered via the airway, information about the location and size of lesion can be acquired quickly and accurately with a less dosage of the fluorescent contrast agent as compared to intravenous administration, and the lesion site can be clearly distinguished from the normal site, and have completed the present disclosure.

Although imaging-assisted cancer detection using a fluorescent contrast agent is studied a lot, the intravenous administration of a fluorescent contrast agent has the problems that the fluorescent contrast agent is distributed throughout the body and the cancer detection rate is relatively low due to the EPR (enhanced permeability and retention) effect. In addition, there are problems that the fluorescent contrast agent has to be administered at a high concentration of 5 mg/kg or higher and the administration dosage has to be in proportion to tumor size.

In a specific example of the present disclosure, after airway administration of ICG to a normal mouse via respiration, the distribution of ICG and the change in fluorescence intensity with time were monitored. As a result, it was found out that an overwhelming amount of the ICG administered via the airway was present the lungs and it was almost nonexistent in other organs such as the brain, spleen, kidneys, etc. In addition, the ICG administered via the airway was distributed in the lungs and showed fluorescence quickly after the administration. It emitted the strongest fluorescence 1 hour after the administration. The fluorescence was maintained for 24 hours after the administration although the intensity decreased gradually (see Example 1). From this result, it can be seen that the airway administration of ICG according to the present disclosure allows faster acquisition of fluorescence images of the lungs as compared to the existing intravenous administration, with no or little effect on other organs.

Also, in a specific example of the present disclosure, in order to investigate whether the airway administration of ICG is actually suitable for cancer detection, fluorescence images and H&E staining images acquired from a lung tumor-induced animal model after airway administration of ICG were compared. As a result, it was confirmed that the fluorescence images acquired after the airway administration of ICG showed consistence in the boundary of cancer tissue with the histological outcome. Thus, it was confirmed that the airway administration of ICG is suitable for cancer detection (Example 2).

Therefore, the present disclosure can provide a pharmaceutical composition for inhalation administration for labeling pulmonary tumorous lesion, which contains a fluorescent contrast agent as an active ingredient, and a kit and an inhalant containing the pharmaceutical composition.

In addition, the present disclosure can provide a method for providing information for determining the presence of lung tumor or determining a pulmonary tumorous lesion site before or during surgery, which includes a step of administering ICG via the airway of a subject, and a method for providing information about the size, location and boundary of lesion during surgery for pulmonary nodules. The information provided by the method may be information for diagnosis and, in this case, it may be provided for diagnosis of lung tumor or monitoring of lung tumor.

Also, in a specific example of the present disclosure, in order to investigate whether the airway administration of ICG can exhibit effect at a lower concentration as compared to intravenous administration, after administering ICG at different concentrations to a lung tumor-induced animal model via the airway, fluorescence images were acquired and cancer detection rate depending on the concentration was investigated. As a result, it was confirmed that, whereas intravenous administration required at least 5 mg/kg of ICG, the boundary between cancer tissue and normal tissue could be distinguished even with 0.1 mg/kg for airway administration.

The administration dosage of Indocyanine green in the airway administration of a fluorescent contrast agent according to the present disclosure may be 0.1-1 mg, specifically 0.1-0.5 mg, more specifically 0.25 mg, per unit body weight (1 kg) of a subject. If the dosage of the administered fluorescent contrast agent is less than 0.1 mg/kg, it is difficult to clearly distinguish the boundary of cancer. And, if it is more than 1 mg/kg, the possibility of allergic reactions is increased.

Also, in a specific example of the present disclosure, in order to investigate whether the airway administration of ICG provides information for determining the boundary of cancer tissue more effectively at a lower concentration than intravenous administration, images were acquired for a group wherein ICG was administered to a lung tumor-induced animal model via the airway and a group wherein ICG was administered by intravenous injection and cancer detection rate was compared. As a result, it was confirmed that, even though the administration dosage of ICG was about 20 times larger for the intravenous administration than the airway administration, the cancer detection rate (TMDE) was about 2.5 times or higher for the airway administration (see Example 4).

Also, in a specific example of the present disclosure, the location and size of lesion could be identified accurately when ICG was administered via the bronchus to the lungs of a patient with lung tumor. It was also confirmed that the present disclosure is suitable for surgery for pulmonary nodules using a fluorescence imaging system (see Example 5).

In the present disclosure, the term "diagnosis" includes any action of, by administrating a fluorescent contrast agent via the airway, determining the presence of damaged or deformed alveoli, determining the boundary between damaged tissue and normal tissue in the lungs, or identifying the status of lung disease based on the size and/or location information of the damaged tissue. The damaged tissue refers to a tissue deformed to such an extent that alveoli cannot function normally. The deformation may be due to pneumothorax and may be caused by foreign materials, abnormally proliferating cell mass, etc., although not being limited thereto.

In the present disclosure, the term "pharmaceutical composition" refers to one prepared for diagnosis of a disease. It may be formulated into various forms according to common methods. Specifically, it may be formulated into an inhalable form. However, the formulation is not limited as long as the composition of the present disclosure can reach alveoli via the airway. In the present disclosure, "inhalation administration" refers to administration of a drug through the nose or mouth of a subject via respiration. Because the inhalation administered drug is delivered to alveoli via the airway, airway administration and inhalation administration may be used interchangeably in the present specification.

Depending on the particular formulation, a pharmaceutically acceptable carrier known in the art, e.g., a buffer, a preservative, a pain reliever, a solubilizer, an isotonic agent, a stabilizer, a base, an excipient, a lubricant, etc. may be further included in the composition.

The pharmaceutical composition of the present disclosure may be administered in a pharmaceutically effective amount. In the present disclosure, the term "pharmaceutically effective amount" refers to an amount sufficient to treat a disease at a reasonable benefit/risk ratio applicable to medical treatment without causing side effects. The level of effective amount may be determined depending on the health condition of a patient, severity of a disease, activity of a drug, sensitivity to the drug, administration method, administration time, administration route, excretion rate, treatment period, drugs used together or concomitantly and other factors well known in the medical field.

Accordingly, the pharmaceutical composition of the present disclosure may be administered to a subject for diagnosis of cancer. In the present disclosure, the tumor refers specifically to lung tumor.

In the present disclosure, the "subject" may be a mammal such as rat, livestock, human, etc. Specifically, it may be human.

The pharmaceutical composition of the present disclosure may be formulated into various forms for administration to a subject. The formulation includes aerosolization.

When the pharmaceutical composition of the present disclosure is provided as an aerosol, the pharmaceutical composition includes an aqueous composition, a dried powder composition, and a propellant-based composition. The present disclosure also provides a kit for labeling pulmonary tumorous lesion, which contains the pharmaceutical composition.

In the present disclosure, the "inhalant" refers to a formulation prepared into an inhalable form and may include an aqueous solution, a dried powder, or a mixture of one or more pharmaceutically acceptable propellant and carrier.

In addition, the pharmaceutical composition of the present disclosure may further contain an adjuvant such as an antiseptic, a hydration agent, an emulsion accelerator, a salt or buffer for control of osmotic pressure, and other therapeutically useful substances.

The pharmaceutical composition according to the present disclosure may be administered to human and animals via the airway. In the present disclosure, the pharmaceutical composition is for inhalation administration. The airway administration includes administration via the nose or mouth, and a nebulizer may be used to help the administration.

In the pharmaceutical composition of the present disclosure, the total effective amount of the fluorescent contrast agent according to the present disclosure may be administered to a patient as a single dose, although not being limited thereto. The content of the active ingredient in the pharmaceutical composition of the present disclosure may vary depending on the severity of the disease. In general, it may be administered repeatedly several times a day, with an effective dose of 6-60 mg for single administration. However, the effective administration dosage of Indocyanine green may be determined in consideration of various factors such as the age, body weight, health condition, sex and diet of the patient, excretion rate, etc. The administration dosage may be specifically 0.1-1 mg, more specifically 0.1-0.5 mg, per unit body weight (1 kg) of the patient.

The pharmaceutical composition of the present disclosure may further contain, in addition to the Indocyanine green as the active ingredient, a known fluorescent contrast agent and may be used in combination with other known diagnostic methods for acquisition of detailed information about pulmonary lesion.

In the present disclosure, the "fluorescent contrast agent" refers to a substance capable of staining living cells or tissues by emitting fluorescence. In the present disclosure, the fluorescent contrast agent may emit near-infrared fluorescence. The near-infrared refers to a region of short wavelength in the infrared region. In general, it may refer to a wavelength range of bout 1.5 to 0.75 µm, although not being limited thereto. Because the near-infrared light penetrates skin better than the visible light, it can be advantageously used to acquire molecular images of blood vessels in the subcutaneous layer, organs, etc. or to guide sensitive parts during surgery.

In the present disclosure, the fluorescent contrast agent is not limited as long as it can provide an optical image by emitting fluorescence. Non-limiting examples include Indocyanine green (ICG), Alexa Fluor 647, Alexa Fluor 660, Alexa Fluor 680, Alexa Fluor 700, Alexa Fluor 780, cy3.5, cy5, cy5.5, cy7, Cypate, ITCC, NIR820, NIR2, IRDye78, IRDye80, IRDye82, IRDye680, IRDye700, IRDye800, DiD, DiR, Cresy Violet, Nile Blue, Oxazine 750, Rhodamine800, Texas Red, etc. Specifically, the fluorescent dye of the present disclosure may be a near-infrared fluorescent dye exhibiting amphiphilicity. It may be selected from a group consisting of cyanine dyes such as cy3.5, cy5, cy5.5 and cy7, ICG, Cypate, ITCC, NIR820, NIR2, IRDye78, IRDye80, IRDye82, oxazine dyes such as Cresy Violet, Nile Blue and Oxazine 750, rhodamine dyes such as Rhodamine800 and Texas Red, and a mixture or complex thereof, although not being limited thereto. More specifically, it may be Indocyanine green.

If the fluorescent contrast agent of the present disclosure is a near-infrared fluorescent dye, it exhibits fluorescence in the near-infrared wavelength range. Accordingly, the composition of the present disclosure may be used to acquire image through the near-infrared (NIR) fluorescence imaging known to those skilled in the art. For example, images may be obtained using a near-infrared optical imaging system and near-infrared fluorescence spectra may be used using a fluorescence spectrophotometer, although not being limited thereto.

The present disclosure can be changed variously and can have various examples. Hereinafter, specific examples are described in detail. However, the present disclosure is not limited by the specific examples, and they should be understood to encompass all changes, equivalents and substitutes included in the technical idea and scope of the present disclosure. In describing the present disclosure, detailed description of related well-known technologies are omitted in order not to obscure the subject matter of the present disclosure.

EXAMPLES

Example 1. Investigation of Distribution of ICG Administered to Normal Animal Model Via Airway and Fluorescence Duration It was investigated, when Indocyanine green (ICG) is administered via the airway of a subject through respiration, whether the lungs are stained properly, organs other than the lungs are also affected, how long the staining lasts, etc. More specifically, 0.25 mg/mL ICG were administered to normal mice for 10 minutes through respiration using the SciReq nebulizer, as shown in FIG. 1a. The, the ICG (2.5 mg/kg)-administered mice were sacrificed 10 minutes, 1 hour, 3 hours, 6 hours and 24 hours later. After extracting the brain, lung, liver, kidney and spleen, fluorescence images were acquired and fluorescence signal intensity was measured using a fluorescence imaging system.

As shown in FIG. 1b, the ICG administered via the bronchus through respiration was present at high concentrations particularly in the lung, and was almost nonexistent in the kidney and spleen. Thus, it was confirmed that the airway administration of ICG is effective for staining of the lungs. In addition, for the airway administration of ICG through respiration for lung staining, very intense fluorescence signals could be detected immediately after the administration. The peak signals were obtained 1 hour after the administration, and the fluorescence signals could be detected even 24 hours after the administration. The boundary between normal tissue and abnormal tissue in the lung could be detected within short time after the administration, and the labeling of the boundary could be maintained for a long time.

Example 2. Identification of Boundary of Cancer Tissue in Lung Tumor-Induced Rabbit Model Through Airway Administration of ICG In Example 1, it was confirmed that the ICG administered via the airway through respiration stained the lung tissue quickly and emitted strong fluorescence with little effect on other organs. Then, it was investigated whether the airway administration of ICG can be used to distinguish cancer tissue from normal tissue by staining only the normal tissue in a lung tumor animal model. Specifically, a lung tumor-induced rabbit model was prepared as shown in FIG. 2 by transplanting VX2 carcinoma into the lungs of a rabbit. The rabbit was made to inhale ICG (0.75 mg/mL) for 4 minutes by connecting a nebulizer to a ventilator. 1 hour later, the chest of the rabbit was cut open and the fluorescence images of the lung were acquired using a NIR imaging system. After conducting surgery for pulmonary nodules, the excised lung tissue was prepared into 10 μm-thick cryosections and optical images were acquired using a NIR microscope. Then, the lung tissue was stained with H&E, and the boundary of cancer tissue was observed histologically.

As shown in FIG. 2b, it was confirmed that the ICG administered through respiration is not distributed in the cancer tissue but stains the normal tissue only, thereby clearly labeling the boundary of cancer tissue. The diameter of the cancer tissue negatively contrasted by ICG was 2 mm, and the boundary of cancer tissue identified by ICG was consistent with the histologically observed boundary of cancer.

In order to investigate the boundary of cancer cells and ICG distribution more accurately, a mouse lung cancer model was established by labeling lung cancer cells with GFP and the distribution of ICG administered through respiration was investigated by fluorescence imaging. As shown in FIG. 2c, it was confirmed that the administered ICG was distributed through the lungs except for the lung cancer cells exhibiting no GFP signal.

Example 3. Comparison of Cancer Detection Rate in Lung Tumor-Induced Rabbit Model Depending on Concentration of Administered ICG It was investigated whether the desired effect can be achieved with a less amount of ICG administered by airway administration as compared to intravenous administration of ICG. Specifically, after administering ICG at different concentrations (0.1 mg/kg, 0.25 mg/kg, 0.5 mg/kg, 1 mg/kg) in the same manner as in Example 2 to the lung tumor-induced rabbit model of Example 2, the fluorescence images of the lung were acquired and TMDE (tumor margin detection efficiency) depending on the ICG concentration was compared.

As shown in FIG. 3, it was confirmed that the boundary of cancer tissue could be detected effectively by airway administration of ICG at 0.1 mg/kg, 0.25 mg/kg, 0.5 mg/kg and 1 mg/kg, and that lung tumor detection rate was increased depending on the concentration of ICG. It was also confirmed that the ICG should be administered at a concentration of 0.25 mg/kg or higher for accurate detection of the boundary of lung tumor.

Example 4. Comparison of Cancer Detection Rate in Lung Tumor-Induced Rabbit Model Depending on Administration Route of ICG Then, it was investigated whether airway administration allows more effective detection of lung tumor lesion as compared to intravenous administration of ICG. Specifically, after extracting the lungs from a lung tumor-induced rabbit model to which 0.25 mg/kg ICG was administered through respiration in the same manner as in Example 2 and a lung tumor-induced rabbit model to which 5 mg/kg ICG was administered intravenously, fluorescence images were acquired and TMDE was quantitated 1 hour later, 3 hours later, 6 hours later and 24 hours later using a NIR imaging system.

As shown in FIG. 4a and FIG. 4b, it was confirmed that the ICG administered through respiration exhibited cancer detection rate of about 2.5 times or higher as compared to the intravenous administration, although the administration dosage was 20 times less.

Example 5. Visualization of Lesion in Human Lungs Through Administration of ICG Via Bronchus As confirmed in Examples 2-4, remarkably high cancer detection rate could be achieved through airway administration of ICG for lung tumor even with a less amount of ICG. In this example, it was investigated whether the airway administration of ICG exhibits the same effect in the actual human lungs and, thus, is suitable for surgery for pulmonary nodules. Specifically, the lobar bronchi of six lung tumor patients who received surgery for pulmonary nodules in Korea University Guro Hospital were connected with tubes and 0.75 mg/mL ICG was administered for 4 minutes using a nebulizer. Then, fluorescence images were acquired using a NIR imaging system. Detailed information of the patients is given in Table 1.

TABLE 1

| Patient | Sex | Age | pTNM Staging | Tumor Size | Pathology Type | Depth (cm) | Invasion to visceral pleura | Surgical Procedure | TMDE |
|---|---|---|---|---|---|---|---|---|---|
| Case 1 | M | 56 | pT1bN2 | 2.2 | Adenocarcinoma | 1.0 | N | RLL lobectomy | 2.8 |
| Case 2 | M | 64 | pT2N0 | 2.4 | Adenocarcinoma | 1.0 | Y | LUL lobectomy | 2.7 |
| Case 3 | F | 52 | pT3N2 | 1.3 | Adenocarcinoma | 0.2 | Y | RUL lobectomy | 3.3 |
| Case 4 | F | 65 | pT2aN0 | 3.1 | Adenocarcinoma | 0.5 | Y | RML lobectomy | 2.6 |
| Case 5 | F | 48 | pT2aN0 | 2.1 | Pleomorphic carcinoma | 0 | Y | RUL lobectomy | 3.4 |
| Case 6 | F | 64 | pT2aN0 | 2.8 | Adenocarcinoma | 0.2 | Y | RUL lobectomy | 2.8 |

As shown in FIG. 5, the inhaled ICG was distributed only in the normal tissue of the lungs and the boundary between cancer tissue and normal tissue was observed distinctly. This result was consistent with the pathological outcome for each patient. Accordingly, it can be seen that the airway administration of ICG is effective for providing information about the location and size of cancer tissue in surgery for pulmonary nodules.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

The invention claimed is:

1. A method for selectively excising a damaged alveolar structure during surgery for pulmonary nodules, comprising:
   (1) a step of administering a fluorescent contrast agent via respiration of a subject;
   (2) a step of cutting open the chest of the subject and detecting a fluorescence signal generated by the contrast agent using a fluorescence imaging system; and
   (3) a step of excising a region where the fluorescence signal is not detected, which is the damaged alveolar structure.

2. The method according to claim 1, wherein the fluorescent contrast agent is one or more selected from a group consisting of Indocyanine green (ICG), Alexa Fluor 647, Alexa Fluor 660, Alexa Fluor 680, Alexa Fluor 700, Alexa Fluor 780, cy3.5, cy5, cy5.5, cy7, Cypate, ITCC, NIR820, NIR2, IRDye78, IRDye80, IRDye82, IRDye680, IRDye700, IRDye800, DiD, DiR, Cresy Violet, Nile Blue, Oxazine 750, Rhodamine800, Texas Red and a mixture thereof.

3. The method according to claim 1, wherein, in the step (1), the fluorescent contrast agent is administered in an amount of 0.1-1 mg per unit body weight (1 kg) of the subject.

4. The method according to claim 1, wherein the administration in the step (1) is performed using a nebulizer.

5. The method according to claim 1, wherein the detecting the fluorescence signal is conducted 10 minutes to 6 hours after the administering the fluorescent contrast agent.

* * * * *